United States Patent [19]

Schmid

[11] Patent Number: 4,586,377
[45] Date of Patent: May 6, 1986

[54] DUAL ACCELEROMETER, METHOD FOR ITS FABRICATION AND APPLICATION THEREOF

[75] Inventor: Felix Schmid, Villars-sur-Glâne, Switzerland

[73] Assignee: Vibro-Meter SA, Fribourg, Switzerland

[21] Appl. No.: 581,906

[22] Filed: Feb. 21, 1984

[30] Foreign Application Priority Data

Feb. 21, 1983 [EP] European Pat. Off. ............ 83810073

[51] Int. Cl.⁴ .............................................. G01P 15/09
[52] U.S. Cl. ..................... 73/517 R; 73/1 D; 73/1 DV; 73/654; 310/329
[58] Field of Search ............... 73/517 R, 654, 1 D, 73/1 DV; 310/329

[56] References Cited

U.S. PATENT DOCUMENTS

| | | | |
|---|---|---|---|
| 3,120,622 | 2/1964 | Dranetz et al. | .................. 73/1 DV |
| 3,566,163 | 2/1971 | Fischer et al. | . |
| 3,727,084 | 4/1973 | Epstein | . |
| 3,744,322 | 7/1973 | Pacey et al. | . |
| 4,213,144 | 7/1980 | Cochard | . |

FOREIGN PATENT DOCUMENTS 1523205 11/1966 Fed. Rep. of Germany .
527665 9/1976 U.S.S.R. ........................... 73/517 R Primary Examiner—Stewart J. Levy
Assistant Examiner—John E. Chapman, Jr.
Attorney, Agent, or Firm—Wender Murase & White

[57] ABSTRACT

The accelerometer comprising two piezoelectric transducers. A common outer seismic mass acts on both transducers and an additional seismic mass acts only on the inner transducer. The sensitivity of the two transducers and the inertial forces acting thereof are so selected that the two transducers, under the action of an acceleration force, each deliver equal output signals. Both seismic masses are accessible for being tuned, in their assembled condition, prior to being mounted in a housing of the accelerometer. The accelerometer requires less material, is of small volume and lightweight, and is particularly suitable for being mounted in aircraft engines. It is also easy to manufacture.

21 Claims, 2 Drawing Figures

DUAL ACCELEROMETER, METHOD FOR ITS FABRICATION AND APPLICATION THEREOF

BACKGROUND OF THE INVENTION

1. Field of the Invention

The present invention relates to a dual accelerometer which comprises a mounting base and two electromechanical transducers arranged one upon the other in between the mounting base and a common seismic mass and an additional seismic mass between the two transducers.

2. Background and Prior Art

Accelerometers are known in which the axis of sensitivity of dual transducers are mutually perpendicular, whereby the transducers measure components of acceleration in mutually perpendicular directions. The adjustment of both transducers to the same sensitivity is achieved by forming each transducer from a relatively high number of individual peizoelectric elements. The number and the individual sensitivity of the elements being so matched and selected that both transducers have the same sensitivity. The precision of the matching of the sensitivities of such transducers is very limited since the sensitivity of each individual transducer may vary during the manufacturing process. This sensitivity matching procedure not only makes transducer manufacture difficult, it also requires the utilization of a relatively high number of piezoelectric elements in each transducer so that the production of an accelerometer based on this method becomes expensive.

U.S. Pat. No. 4,213,114 discloses the use of two identical accelerometers, each with the same axis of sensitivity, that is monoaxial accelerometers, for controlling vibrations of rotating machines, such as aircraft engines. Each transducer of such accelerometers is connected to an independent measuring circuit in order to improve the redundancy of the measuring device. Unfortunately, this construction results in a relatively expensive, voluminous and heavy device. In order to be mounted in aircraft engines, accelerometers should preferably have small dimensions and be of light weight.

U.S. Pat. No. 3,744,322 discloses the use of an angular velocity sensor utilizing the Coriolis force. The sensor comprises two proof masses arranged between piezoelectric transducers. These transducers are excited by an a.c. signal having a frequency of 5 kHz which functions to set the masses into vibration along the axis of rotation of the sensor. The movements of the masses along the axis of rotation are 180° out of phase with one another. The device further comprises pairs of sensors sensitive to shear forces in two directions perpendicular to one another and to the axis of rotation of the sensor. However, such an angular velocity sensor does not include an additional seismic mass between the transducers so that the sensitivity of the transducers may be easily matched to deliver a signal of desired value when both transducers are submitted to a common acceleration.

SUMMARY OF THE INVENTION

An object of the present invention is to provide a dual accelerometer with transducers having matched sensitivities of a desired value, able to be easily manufactured and having a small volume and weight. To achieve this and other objects, an accelerometer according to the present invention comprises dual transducers having a common seismic mass and an additional seismic mass arranged between the dual transducers, the masses and the sensitivities of the transducers being so adjusted in relation to one another that for a common acceleration, both transducers deliver signals of a predetermined value under the action of the inertial forces. In this case, the two seismic masses may be so selected that even with a very small number of piezoelectric elements, both transducers may be adjusted to have essentially the same sensitivity. Preferably, the transducer on which only the common seismic mass acts comprises only two piezoelectric elements while the transducer on which both the common and additional seismic masses as well as the mass of the transducer lying between these masses acts, preferably comprises only a single piezoelectric element. A fine adjustment of the sensitivity of both transducers is also possible in that the common mass and the additional mass may be machined off. Due to this adjustment capability, it is possible to utilize a very small number of piezoelectric elements of highly sensitive peizoelectric material so that despite the additional seismic mass, a reduction in volume and weight may be achieved.

The invention will be further described by way of example and with reference to the accompanying drawings.

DESCRIPTION OF THE PREFERRED EMBODIMENT

Figure 1:
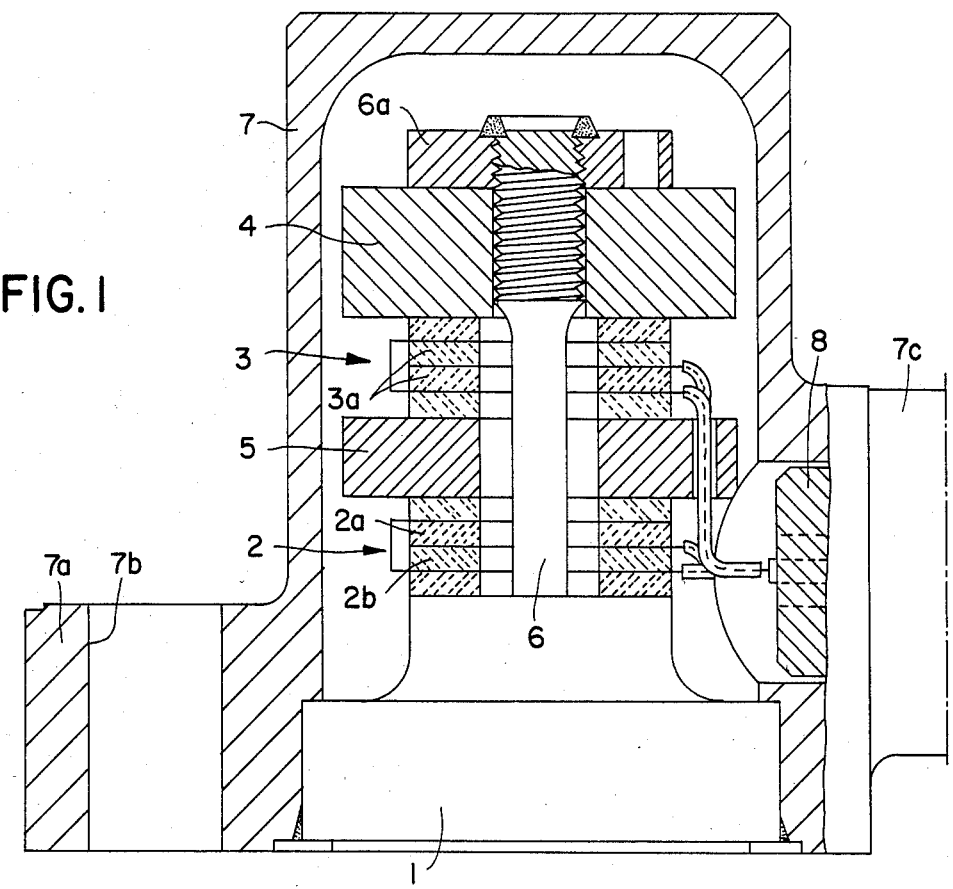
FIG. 1 is an elevational view of an accelerometer in partial section.

The active part of the accelerometer comprises a mounting base 1, a first piezoelectric transducer 2, a second piezoelectric transducer 3, a common seismic mass 4, an additional seismic mass 5 arranged between the transducers 2 and 3 and a bolt 6 for firmly connecting the mounting base 1 to the seismic mass 5. The bolt 6 is anchored in the mounting base 1 and a nut 6a is screwed at the upper end of the bolt 6 and welded in its tightened condition thus prestressing the transducers 2 and 3 and the seismic mass 4 and 5 such that for all possible accelerations, only pressure forces will act on these elements. The active parts of the accelerometer are mounted by means of the mounting base 1 in a housing 7 having flange 7a with, for example, three mounting holes 7b.

The lower transducer 2 comprises a single piezoelectric element and a ferroelectric element 2b. These two elements are sandwiched between a pair of unnumbered insulation discs. The transducer 3 comprises two piezoelectric elements 3a sandwiched between a pair of unnumbered insulation discs. The connections of the transducer 3 are preferably channeled through a hole in the additional mass 5. All external connections are channeled through a hermetically sealed closing piece 8, under insulation, through a support 7c of the housing 7. The remaining internal connections and terminals of both transducers 2 and 3 are only schematically indicated. The transducer 3 preferably has a sensitivity practically twice as great as the transducer 2. Due to the ferroelectric disc 2b, the capacitive characteristics of both transducers are identical so that potential electrical interference is reduced to a minimum, and will have the same influence on both transducers. A flexible electrical connection between seismic mass 5 and the mounting base 1 insures that the electrical potential of the seismic masses 4 and 5 and the mounting base is the same as that of the housing 7 thereby avoiding any disturbing influence from electrostatic fields, and at the same time screening the transducers 4 and 5. The hermetically sealed electrical connections through the closing piece 8 protects the transducers against environmental influences.

As alluded to above, the transducer 3 has a sensitivity about twice as great as the transducer 2. In the presence of an acceleration, only those inertial forces due to the seismic mass 4 act on the transducer 3 while the inertial forces of both seismic masses 4 and 5 as well as that of the transducer 3 act on the transducer 2. The additional seismic mass 5 is therefore selected so that together with the mass of the transducer 3, it becomes about the same as the seismic mass 4. Thus, the inertial forces acting on the transducer 2 are about twice as great as the inertial forces acting on transducer 3. Consequently, for an acceleration of a determined magnitude, the transducers 2 and 3 will each deliver electrical signals of substantially the same value. Adjustment to essentially identical output signals may be achieved during fabrication, before the transducers and seismic masses., i.e., active parts, are introduced in the housing 7. After the active parts have been screwed and prestressed, the signals of the two transducers may be measured and compared under predetermined conditions. By adjusting (e.g., machining away) the mass of the common seismic mass 4, the sensitivity of the transducer 3 may be brought to the desired value. Then, the additional seismic mass 5 may be adjusted (e.g., machined away) in order to adjust the sensitivity of the transducer 2 so that both transducers deliver identical signals under the same conditions. The active parts are then mounted in the housing 7.

Figure 2:
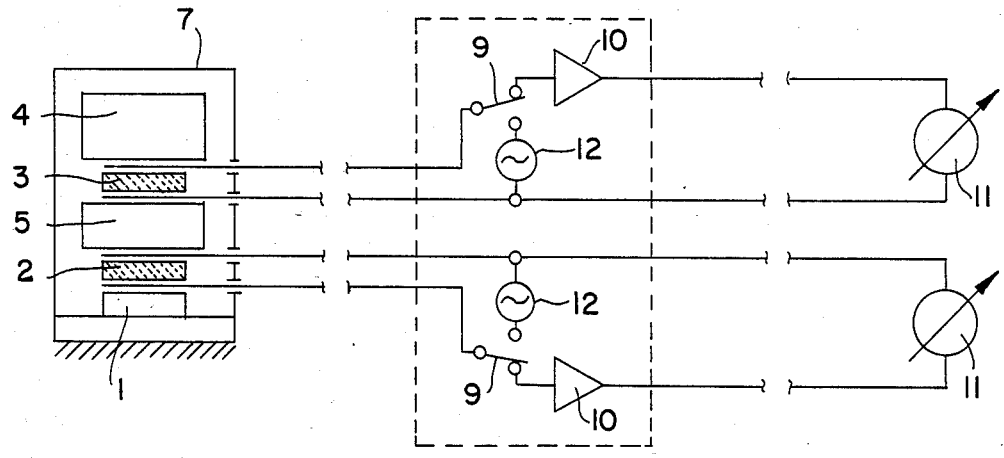
FIG. 2 is a schematic diagram at a circuit utilizing the accelerometer of FIG. 1.

In the descriptions and in the claims, it is assumed and indicated that both transducers have matching sensitivities. As used herein, this is intended to mean that under predetermined conditions, the two transducers will deliver essentially matching output signals. This signal matching is essential for the above indicated connection of the accelerometer into a measuring circuit with two channels. Such a circuit is schematically indicated in FIG. 2 in which the accelerometer with its essential parts is also schematically illustrated. Corresponding parts bear the same reference numbers as in FIG. 1. The two transducers 2 and 3 are each connected to a measuring instrument 11 through a change-over switch 9 and an amplifier 10. Under normal conditions the measuring instruments 11 each indicate the same value of acceleration under the same value of vibration. Such indications, within a normal range, indicates that the accelerometer, as well as the measuring circuits, are working normally. Different indications from the instruments 11 indicate that either one of the transducers 2 or 3 or one of the amplifiers 10 is not working normally.

It is desirable that during engine shut down, i.e., in the absence of any acceleration or vibration, an operator be able to control the operating ability of the system. To this end, each of the change-over switches 9 may be switched to connect one of the generators 12 into the circuit. The generators 12 produce signals having an adequate amplitude and frequency to excite the transducers. If one of the change-over switches 9 is switched to connect a generator 12 into the circuit, the corresponding transducer receives the output of the generator 12 and it then functions as a driving electromechanical transducer, the oscillation of which is delivered to the other transducer. The other transducer, which is connected as previously described to its amplifier 10 and its measuring instrument 11, then generates a signal indicating if both transducers, and the working channel, are working normally. If this is the case, the operation can then switch over so that the other transducer is connected with the corresponding generator 12 and the transducer which was previously connected with is corresponding generator is connected with its measuring channel. This permits a complete check of both transducers as well as of the entire accelerometer and the two measuring channels in the shut down condition. The precise adjustment of the transducers 2 and 3 for the same sensitivity, and for the same output signals is particularly important in the case of a circuit like that of FIG. 2, since in the event of a failure of the circuit, a replacement circuit must be inserted without any need for adjustment.

Various embodiments are possible. The number of piezoelectric elements in both transducers may be different from those indicated above provided the seismic masses are correspondingly adapted. However, for the above-indicated reasons, there exists an interest in reducing the number of piezoelectric elements to a minimum. In the above indicated embodiment, it is assumed that both transducers 2 and 3 work monoacially which means that their axis of sensitivity is the same as the axis of the bolt 6. However, it would also be possible to provide transducers having perpendicular axis of sensitivity. In this way, one of the transducers would be sensitive to pressure and the other to shear. Each transducers could also have a maximum shear sensitivity in mutually perpendicular directions.

The simplicity of the active parts utilized in the described embodiment is essential. The seismic masses 4 and 5 are preferably simple metallic rings of steel or other suitable material. It is also a particularly important feature that both masses, even in their mounted condition, be easily accessible in order to be adjusted or machined for purposes of mass selection. In a preferred embodiment, these masses may also be rotated easily. In an alternative embodiment, the masses would be accessible only in the mounted condition for purposes of adjustment.

It is also necessary to ensure that the prestressing of the transducers is not dependent upon temperature. To this end, at least one of the seismic masses 4 or 5 preferably comprises a material having a thermal dilatation such that the mechanical prestressing of the device remains constant over the whole temperature working range.

I claim:

1. A dual accelerometer having first and second output channels and comprising:
    a mounting base;
    a first electro-mechanical transducer having a first sensitivity;
    a second electro-mechanical transducer having a second sensitivity;
    a first seismic mass acting on both of said first and second electro-mechanical transducers, said first and second electro-mechanical transducers being disposed between the mounting base and said first seismic mass; and
    a second seismic mass disposed between said first and second electro-mechanical transducers, said first and second seismic masses and said first and second sensitivities being relatively selected so that for a common acceleration each of said first and second output channels carry signals of essentially the same value.

2. The dual accelerometer according to claim 1, wherein said first and second transducers are formed from piezoelectric elements, and wherein said first transducer is disposed between said mounting base and said second seismic mass and is formed from fewer piezoelectric elements than said second transducer.

3. The dual accelerometer according to claim 2, further comprising means for mounting said first and second transducers and said first and second seismic masses on said mounting base, and wherein said seismic masses may be adjusted while mounted on said mounting means for essentially equalizing the output signals of said first and second transducers.

4. The dual accelerometer according to claim 3, wherein said first transducer comprises one piezoelectric element less than said second transducer.

5. The dual accelerometer according to claim 4, wherein said second transducer comprises two piezoelectric elements and said first transducer comprises one piezoelectric element.

6. The dual accelerometer according to claim 5, wherein said first transducer further comprises an element formed of ferroelectric material.

7. The dual accelerometer according to claim 3, wherein said mounting means comprises a bolt, passing through said electro-mechanical transducers and said seismic masses, and anchored in said mounting base.

8. The dual accelerometer according to claim 7 wherein said bolt is operable for prestressing said electromechanical transducers.

9. The dual accelerometer according to claim 1, wherein at least one of the two seismic masses is formed of a material having a predetermined thermal dilation over a predetermined working temperature range such that any mechanical prestressing of either of said electro-mechanical transducers is essentially constant over said predetermined working temperature range.

10. A dual channel accelerometer having two output channels, a mounting base and comprising:
arranged in succession on said mounting base a first electro-mechanical transducer having an axis of sensitivity, a first seismic mass, a second electro-mechanical transducer having an axis of sensitivity, and a second seismic mass;
mounting means for securing together and prestressing against said mounting base said electro-mechanical transducers and said seismic masses, each of said electro-mechanical transducers being connected to one of said output channels and being responsive to an acceleration acting along its axis of sensitivity for delivering a signal to its respective output channel; and
means for indicating the signal on each of said output channels.

11. The dual accelerometer according to claim 10, wherein said dual accelerometer operates within a predetermined operating temperature range, and wherein at least one of said seismic masses is formed of a material having a thermal dilatation such that the prestressing of the transducers and the seismic masses remains constant over said predetermined operating temperature range.

12. A dual accelerometer having two output channels, a mounting base and comprising:
arranged in succession on said mounting base a first electro-mechanical transducer having an axis of sensitivity, a first seismic mass, a second electro-mechanical transducer, and a second seismic mass;
a bolt for securing together and prestressing against said mounting base, said electro-mechanical transducers and said seismic masses, each of said electro-mechanical transducers being connected to one of said output channels and being responsive to an acceleration acting along its axis of sensitivity for delivering a signal to its respective output channel; and
means for indicating the signals from each of said output channels, said first and second electro-mechanical transducers being at least partially formed from piezoelectric elements, said first electro-mechanical transducer having a different sensitivity than said second electro-mechanical transducer.

13. The dual accelerometer according to claim 12, wherein said first transducer further comprises a ferroelectric material element.

14. The dual accelerometer according to claim 12, wherein said dual accelerometer operates within a predetermined operating temperature range, and wherein at least one of said seismic masses is formed of a material having a thermal dilatation such that the prestressing of the transducers and the seismic masses remains constant over said predetermined operating temperature range.

15. The dual accelerometer according to claim 14, wherein the second transducer comprises one piezoelectric element more than the first transducer.

16. The dual accelerometer according to claim 14 wherein the first transducer comprises one piezoelectric element and the second transducer comprises two piezoelectric elements.

17. A dual accelerometer having two output channels, a mounting base and comprising:
arranged in succession on said mounting base a first electro-mechanical transducer having a first sensitivity, a first seismic mass, a second electro-mechanical transducer having a second sensitivity, and a second seismic mass, each of said electro-mechanical transducers being connected to one of said output channels; and
a bolt for securing together and prestressing against said mounting base said first and second transducers and said first and second seismic masses, wherein said first and second sensitivities have relative arbitrary values and said seismic masses are selected to compensate for said arbitrary sensitivity values whereby each of said transducers delivers essentially the same output signal to its respective output channel in response to a predetermined acceleration.

18. In combination:
a dual accelerometer having two output channels, two electro-mechanical transducers each connected to a respective one of said output channels, a first seismic mass acting on both of said electro-mechanical transducers and a second seismic mass disposed between said electromechanical transducers and acting on only one of said electro-mechanical transducers, said first and second seismic masses being selected so that for a common acceleration, each of said output channels nominally carry signals of essentially the same value;

means, connected to said output channels, for measuring and checking the operating condition of said dual accelerometer, said measuring and checking means comprising, for each output channel, a change-over switch, a measuring instrument, and a signal generator;

each of said change-over switches being operable to connect its respective electro-mechanical transducer to its respective signal generator for causing said electro-mechanical transducer to vibrate and for transferring said vibration to the other electro-mechanical transducer wherein the measuring instrument connected to the other electro-mechanical transducer measures the operating condition of both of said electro-mechanical transducers in response to said transferred vibration.

19. In combination:

a dual accelerometer having two output channels and two electro-mechanical transducers, each connected to a respective one of said output channels, a first seismic mass acting on both of said electro-mechanical transducers and a second seismic mass disposed between said electromechanical transducers and acting on only one of said electro-mechanical transducers, said first and second seismic masses being selected so that for a common acceleration, each of said output channels nominally carry signals of essentially the same value;

a measuring device connected to at least one of said output channels;

a signal generator;

means for selectively connecting one of said electro-mechanical transducers to said signal generator for causing one or said electro-mechanical transducers to vibrate and for transferring said vibration to the other of said electromechanical transducers, wherein said measuring device is operable to measure the operating condition of both of said electro-mechanical transducers.

20. A method of calibrating a dual accelerometer having a mounting base comprising the steps of:

arranging in succession on said mounting base a first electro-mechanical transducer, a first seismic mass, a second electro-mechanical transducer, and a second seismic mass;

securing said electro-mechanical transducers and said seismic masses to said mounting base;

prestressing said electro-mechanical transducers and said seismic masses against said mounting base to form said dual accelerometer;

subjecting said dual accelerometer to a predetermined force;

reducing said second seismic mass until said second electro-mechanical transducer delivers a desired output signal in response to said predetermined force;

reducing said first seismic mass until said first electro-mechanical transducer delivers a desired output signal in response to said predetermined force.

21. A method of calibrating a dual accelerometer comprising the steps of:

assembling on a mounting base in succession, a first electro-mechanical transducer, a first seismic mass, a second electro-mechanical transducer, and a second seismic mass;

prestressing said assembled electro-mechanical transducers and seismic masses;

subjecting said dual accelerometer to a predetermined force;

altering said second seismic mass until a desired output signal in response to said predetermined force is obtained from the second electro-mechanical transducer;

altering the first seismic mass until a desired output signal in response to said predetermined force is obtained from the second electro-mechanical transducer.

* * * * *